United States Patent [19]
Mueller et al.

[11] Patent Number: 6,066,131
[45] Date of Patent: May 23, 2000

[54] CONTIGUOUS, BRANCHED TRANSMYOCARDIAL REVASCULARIZATION (TMR) CHANNEL, METHOD AND DEVICE

[75] Inventors: Richard L. Mueller; Stuart D. Harman, both of Sunnyvale; Robert L. Lathrop, Jr.; Bruce J. Richardson, both of San Jose, all of Calif.

[73] Assignee: Eclipse Surgical Technologies, Inc., Sunnyvale, Calif.

[21] Appl. No.: 09/092,798

[22] Filed: Jun. 5, 1998

Related U.S. Application Data

[62] Division of application No. 08/675,698, Jul. 3, 1996, Pat. No. 5,766,164.

[51] Int. Cl.$^7$ .................................................. A61B 17/36
[52] U.S. Cl. .................................. 606/15; 606/7; 607/89
[58] Field of Search ............................. 606/7, 9, 12, 10, 606/14–17, 19; 607/89

[56] References Cited

U.S. PATENT DOCUMENTS

| | | |
|---|---|---|
| 4,029,084 | 6/1977 | Soldner . |
| 4,658,817 | 4/1987 | Hardy . |
| 4,669,465 | 6/1987 | Moore et al. . |
| 4,846,171 | 7/1989 | Kauphusman et al. . |
| 5,125,926 | 6/1992 | Rudko et al. . |
| 5,380,316 | 1/1995 | Aita et al. . |
| 5,389,096 | 2/1995 | Aita et al. . |
| 5,591,159 | 1/1997 | Taheri . |
| 5,662,124 | 9/1997 | Wilk ........................................ 128/898 |
| 5,713,894 | 2/1998 | Murphy-Chutorian et al. . |
| 5,725,523 | 3/1998 | Mueller . |
| 5,738,680 | 4/1998 | Mueller et al. . |
| 5,769,843 | 6/1998 | Abela et al. .............................. 606/10 |

FOREIGN PATENT DOCUMENTS

| | | |
|---|---|---|
| 0515867 A2 | 2/1992 | European Pat. Off. . |
| 0 515 867 A2 | 12/1992 | European Pat. Off. . |
| WO 92/10142 | 6/1992 | WIPO . |
| WO PCT 92/10142 | 6/1992 | WIPO . |
| WO 94/14383 | 7/1994 | WIPO . |
| WO 94/14383 A1 | 7/1994 | WIPO . |
| WO 95/17127 | 6/1995 | WIPO . |

OTHER PUBLICATIONS

Deckelbaum, "Cardiovascular Apps. of Laser Tech.", Lasers in Surgery and Medicine, 15:315–341 (1994).

Frazier et al., "Myocard. Revasc. with Las.", Cullen Cardio. Res. Labs., Tx. Heart Inst., Supp. II C vol. 92, No. 9, II–58–65 (Nov. 1, 1995).

*Primary Examiner*—Francis J. Jaworski
*Attorney, Agent, or Firm*—Ray K. Shahani; Ilene Lapidus Janofsky

[57] ABSTRACT

Improved methods and devices related to laser-assisted transmyocardial revascularization (TMR), and more particularly, to improved methods and devices for creating branched TMR channels through myocardium in which a single opening is made in an epicardial surface with a plurality of channel branches, having predetermined geometries extending into and through myocardium, depending therefrom. A method of creating branched TMR channels comprises piercing an epicardial surface mechanically or with laser energy, directing laser energy through the opening in a first predetermined angular orientation with respect to the epicardial surface to create a first channel and delivering laser energy in a second predetermined angular orientation to create a second branch. A plurality of branches can thus be created in a single channel structure. A guide block device allows an opening to be made in an epicardial surface mechanically or with laser energy and provides a structure for directing laser energy into myocardium in a plurality of channels depending from the opening. Rotating guide devices and finger held devices with rotating head means include a hand held device with an elongated wand-like handle portion, a rotating head portion and a hollow guide needle means. Preferred embodiments further comprise a laser delivery means advancing mechanism and guide needle rotating means.

14 Claims, 14 Drawing Sheets

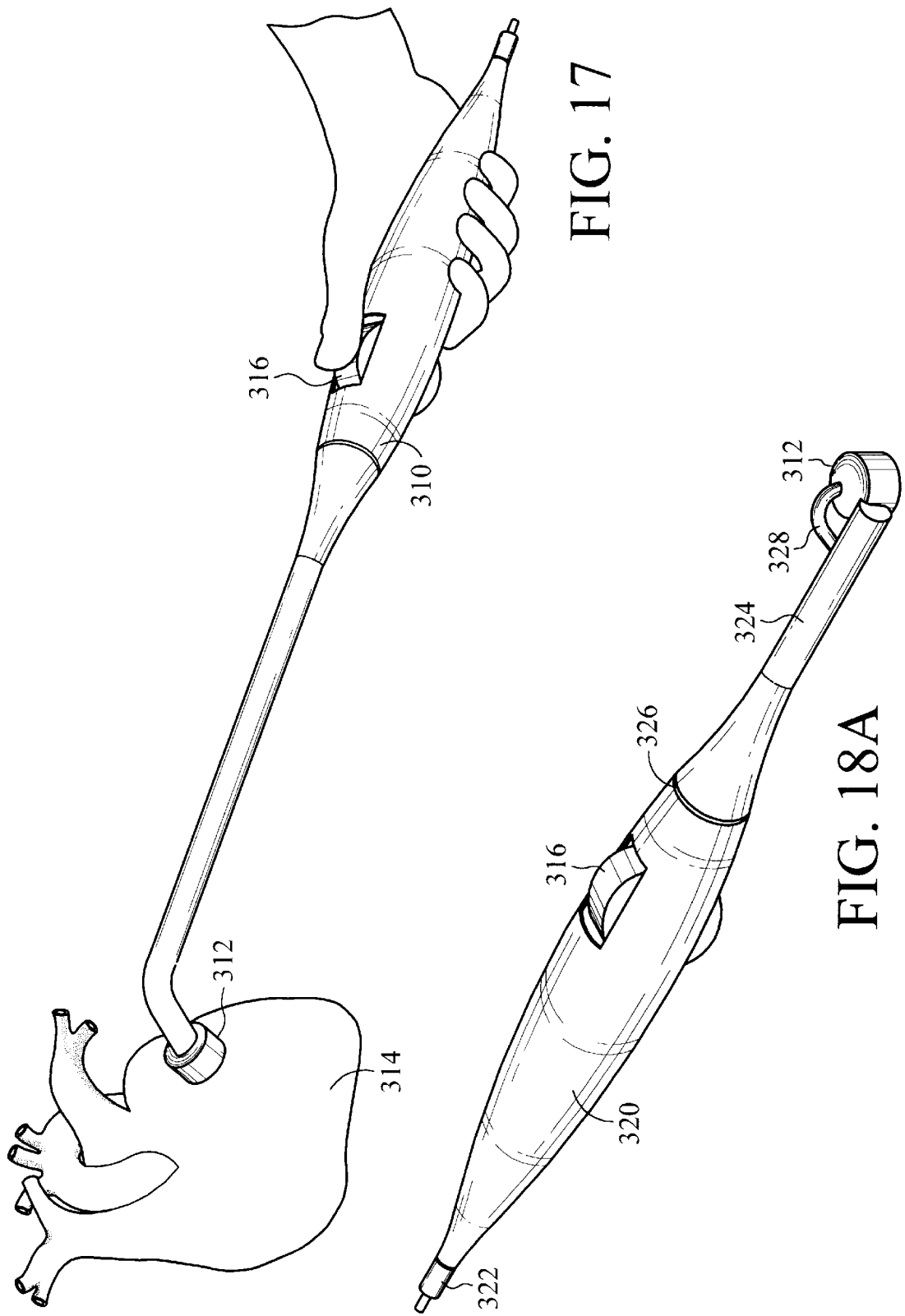

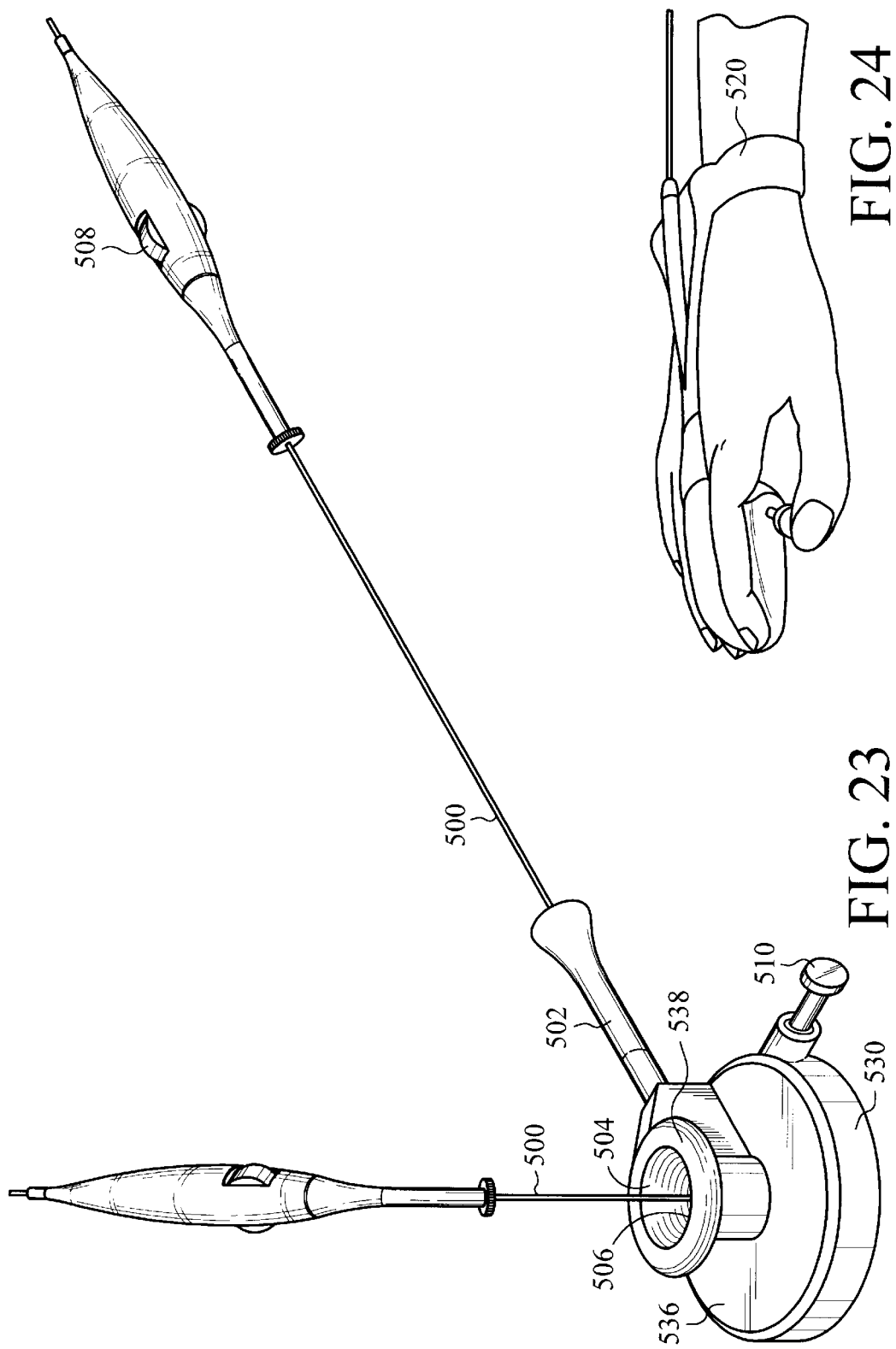

CONTIGUOUS, BRANCHED TRANSMYOCARDIAL REVASCULARIZATION (TMR) CHANNEL, METHOD AND DEVICE

This is a divisional application of Ser. No. 08/675,698 filed Jul. 3, 1996, now U.S. Pat. No. 5,766,164.

FIELD OF THE INVENTION

The present invention relates to a surgical procedure known as laser-assisted transmyocardial revascularization (TMR), and more particularly, to contiguous, branched TMR channels, including methods and devices for creating them, which originate at a single point on or below the epicardial surface and develop along a plurality of radiating, ultimately independent paths thereby permitting capillary communication and enhanced myocardial infusion of oxygenated blood, growth, healing, and other factors. These methods and apparatuses can be adapted for use in surgical applications throughout the human body or in animals for piercing, infusion, vascularization or transmission of laser energy, drugs or other treatment therapies precisely, at predetermined positions and to predetermined depths.

BACKGROUND OF THE INVENTION

Heart disorders are a common cause of death in developed countries. The major cause of heart disease in developed countries is impaired blood supply. The coronary arteries, which supply blood to the heart, become narrowed due to atherosclerosis and part of the heart muscle is deprived of oxygen and other nutrients. The resulting ischemia or blockage can lead to angina pectoris, a pain in the chest, arms or jaw due to a lack of oxygen to the heart, or infarction, death of an area of the myocardium caused by ischemia.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be treated in a number of ways. Drug therapy, including nitrates, beta-blockers, and peripheral vasodilatator drugs (to dilate the arteries) or thrombolytic drugs (to dissolve clots) can be very effective. Transluminal angioplasty is often indicated—the narrowed diameter of the opening or lumen of the artery, clogged with atherosclerotic plaque or other deposits, can be increased by passing a balloon to the site and inflating it. In the event drug therapy is ineffective or angioplasty is too risky, the procedure known as coronary artery bypass grafting (CABG) may be indicated. The procedure requires the surgeon to make an incision down the center of the patient's chest and the heart is exposed by opening the pericardium. A length of vein is removed from another part of the body, typically the leg. The section of vein is first sewn to the aorta and then sewn onto a coronary artery at a place such that oxygenated blood can flow directly into the heart. CABG is a major surgical procedure which requires the installation of the heart-lung machine and the sternum must be sawed through.

Another method of improving myocardial blood supply is called transmyocardial revascularization (TMR), the creation of channels from the epicardial to the endocardial portions of the heart. The procedure using needles in a form of "myocardial acupuncture" has been used clinically since the 1960s. Deckelbaum, L. I., Cardiovascular Applications of Laser Technology, *Lasers in Surgery and Medicine* 15:315–341 (1994). The technique was said to relieve ischemia by allowing blood to pass from the ventricle through the channels either directly into other vessels perforated by the channels or into myocardial sinusoids which connect to the myocardial microcirculation. The procedure has been likened to transforming the human heart into one resembling that of a reptile.

In the reptilian heart, perfusion occurs via communicating channels between the left ventricle and the coronary arteries. Frazier, O. H., Myocardial Revascularization with Laser—Preliminary Findings, *Circulation,* 1995; 92 [suppl II]:II-58–II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial—arterial, arterial-venous, and venous-luminal connections. This vascular mesh forms an important source of myocardial blood supply in reptiles but its role in humans is poorly understood.

Numerous studies have been performed on TMR using lasers to bore channels in the myocardium. Histological evidence of probable new vessel formation adjacent to collagen occluded transmyocardial channels exists. In the case of myocardial acupuncture or boring, which mechanically displaces or removes tissue, acute thrombosis followed by organization and fibrosis of clots is the principal mechanism of channel closure. By contrast, histological evidence of patent, endothelium-lined tracts within the laser-created channels supports the assumption that the lumen of the laser channels is or can become hemocompatible and that it resists occlusion caused by thrombo-activation and/or fibrosis. A thin zone of charring occurs on the periphery of the laser-created transmyocardial channels through the well-known thermal effects of optical radiation on cardiovascular tissue.

U.S. Pat. No. 4,658,817 issued Apr. 21, 1987 to Hardy teaches a method and apparatus for TMR using a laser. A surgical $CO_2$ laser includes a handpiece for directing a laser beam to a desired location. Mounted on the forward end of the handpiece is a hollow needle to be used in surgical applications where the needle perforates a portion of tissue to provide the laser beam direct access to distal tissue.

U.S. Pat. No. 5,125,926 issued Jun. 30, 1992 to Rudko et al. teaches a heart-synchronized pulsed laser system for TMR. The device and method comprises a device for sensing the contraction and expansion of a beating heart. As the heart beat is monitored, the device triggers a pulse of laser energy to be delivered to the heart during a predetermined portion of the heartbeat cycle. This heart-synchronized pulsed laser system is important where the energy and pulse rate of the particular type of laser are potentially damaging to the beating heart.

U.S. Pat. No. 5,380,316 issued Jan. 10, 1995 and U.S. Pat. No. 5,389,096 issued Feb. 14, 1995 both to Aita et al. teach, respectively, systems and methods for intra-operative and percutaneous myocardial revascularization. The '316 patent is related to TMR performed by inserting a portion of an elongated flexible lasing apparatus into the chest cavity of a patient and lasing channels directly through the outer surface of the epicardium into the myocardium tissue. In the '096 patent TMR is performed by guiding an elongated flexible lasing apparatus into a patient's vasculature such that the firing end of the apparatus is adjacent the endocardium. Channels are created directly through the endocardium into the myocardium tissue without perforating the pericardium layer.

TMR is most often used to treat the lower left chamber of the heart. The lower chambers or ventricles are fed by the more distal branches of the coronary arteries. Distal coronary arteries are more prone to blockage and resulting heart muscle damage.

To date, TMR channels have been created surgically straight through the epicardial surface into the myocardium, or in the alternative, vascularly via catheter from the endocardium within a chamber straight radially outwards into myocardium. In either case, an essentially single-ended channel is ultimately formed.

A need exists in the prior art for maintaining patency of TMR channels, for increasing blood flow in channels that are closed at the epicardium, or created percutaneously, for reducing trauma to the epicardial layer of the heart, and for creating multiple channels through a single opening, particularly in areas where access and visibility are limited.

Thus, broadly, it is an object of the present invention to provide an improved method and device for laser-assisted transmyocardial revascularization (TMR).

It is a further object of the present invention to provide a method for performing TMR in which branched channels are created in the myocardium through a single access opening thereby reducing trauma to the exterior of the heart.

It is a further object of the present invention to provide a method for performing TMR in which branched channels are created in the myocardium to allow flow of blood and other factors through channel branches from myocardial capillaries.

It is a further object of the present invention to provide a device for performing TMR in which branched channels are created in the myocardium.

It is a further object of the present invention to provide a device for performing TMR, particularly suitable for use in areas where access and visibility are limited, in which branched channels are created in the myocardium, through a single opening, by providing a fiber advancing mechanism and a laser delivery means having needle orientation means.

It is a further object of the present invention to provide a device for performing TMR in which branched channels are created in the myocardium by providing a hand-held device with a fiber advancing mechanism and a laser delivery means with needle orientation means.

It is a further object of the present invention to provide a device for performing TMR in which branched channels are created in the myocardium by providing a finger-tip operated device with fiber advancing mechanism and a laser delivery means with needle orientation means.

SUMMARY OF THE INVENTION

A transmyocardial revascularization (TMR) channel structure defining a predetermined geometry comprising an opening in an epicardium of a human heart, a first branch extending from the first opening into myocardium, and at least one additional branch into myocardium, the first branch and at least one additional branch in communication with each other. A preferred embodiment of the TMR channel structure has at least one of the additional branches non-contiguous with the first branch at all points other than near the opening. A preferred embodiment of the TMR channel structure further comprises a cavity disposed between and communicating with the first and at least one additional branch. A preferred embodiment of the TMR channel structure further comprises at least two additional branches extending from the first branch into myocardium, thereby creating a plurality of communicating TMR channels in preselected portions of myocardium. A preferred embodiment of the TMR channel structure has at least one branch of the TMR channel arcuate in shape. A preferred embodiment of the TMR channel structure has at least one branch of the TMR channel extending through endocardium.

A method for creating a branched transmyocardial revascularization (TMR) channel in a preselected portion of myocardium, the method comprising the following steps: (a) creating an opening in an epicardial layer of a heart ventricle; (b) delivering a first amount of laser energy through the opening at a first predetermined angle with respect to the epicardial surface so as to create a first branch in myocardium; and (c) delivering a second amount of laser energy through the first opening at a second predetermined angle with respect to an epicardial surface so as to create a second branch in the myocardium, the first and the second predetermined angles being different from each other, the first and the second branches in communication with each other at one or more points, thereby forming a contiguous, branched TMR channel. In a preferred embodiment of the method, step (a) further comprises the step of delivering sufficient laser energy to an epicardial surface to create at least one hole therethrough. A preferred embodiment of the method further comprises the step of delivering sufficient laser energy to at least one branch to penetrate through an endocardial surface. A preferred embodiment of the method further comprises the following step: (d) delivering additional amounts of laser energy through the opening at additional predetermined angles with respect to the epicardial layer to create a plurality of branches in myocardium at angles different from each other, wherein the plurality of branches of the TMR channel so created are in communication with each other to form a contiguous, branched TMR channel.

A method for creating a contiguous, branched transmyocardial revascularization (TMR) channel in a preselected portion of myocardium, the method comprising the following steps: (a) creating an opening in an epicardial layer by mechanical piercing; (b) inserting a hollow guide needle into the opening; (c) delivering a first amount of laser energy through the hollow guide needle at a first predetermined angle with respect to the epicardial layer as determined by an angular orientation of the hollow guide needle, so as to create a first branch of the TMR channel in myocardium; (d) rotating the hollow guide needle within the opening of the epicardial surface to a second predetermined angular orientation; and (e) delivering a second amount of laser energy through the hollow guide needle at a second predetermined angle as determined by the second angular orientation of the hollow guide needle, so as to create a second branch of the TMR channel. A preferred embodiment of the method comprises the following additional step: (f) retracting the laser delivery means such that a distal end of the laser delivery means does not extended past an opening at a distal end of the guide needle prior to the step of delivering a second amount of laser energy through the hollow guide needle at a second predetermined angle. A preferred embodiment of the method in which at least one branch of the TMR channel extends through endocardium.

A guide block device for a surgical transmyocardial revascularization (TMR) procedure, the guide block device comprising a body portion for placement on an epicardial surface of the heart, the body portion having upper and lower surfaces, an opening extending between the upper and lower surfaces, and a bearing surface surrounding and extending from the opening through the body portion and defining pivot-point means for angulation of a laser delivery means to create a contiguous, branched TMR channel. In a preferred embodiment, the guide block device further comprises a hollow guide needle, the guide needle having a proximal end, a central axis, and a distal end sharpened for mechanically piercing an epicardial layer, the hollow guide needle directing the laser delivery means to deliver laser energy to preselected portions of myocardium.

A rotating guide device for creating branched transmyocardial revascularization (TMR) channels in preselected portions of myocardium, the rotating guide device comprising a housing positionable on an epicardial surface adjacent a preselected portion of myocardium, the housing portion having an upper surface, and a lower surface, rotating head means disposed within the housing, hollow guide needle means operatively connected to the rotating head means and having a central axis, a proximal end, and a distal end, the distal end sharpened for mechanically piercing an epicardial layer, wherein the hollow guide needle means directs a laser delivery device for delivery of laser energy through the guide needle means and through the epicardial layer to preselected portions of myocardium at a first predetermined angle with respect to the epicardial layer to create a first branch extending into myocardium, the laser delivery means retractable through the hollow guide needle means and the hollow guide needle means rotatable for delivery of laser energy into myocardium at a second predetermined angle with respect to the epicardial layer to create a second branch, the first and the second branches forming, in combination, a contiguous, branched TMR channel. In a preferred embodiment, the guide needle means of the rotating guide device further comprises a curvature at the distal end so as to deflect the distal end of a laser delivery device to an angle with respect to the central axis of the hollow guide needle means. In a preferred embodiment, the rotating head of the rotating guide device is indexed with a predetermined number of angular positions such that the distal end of the guide needle is directed to a predetermined number of angular positions to allow the laser delivery means to deliver laser energy into myocardium at predetermined angles with respect to an epicardial surface. In a preferred embodiment, the rotating guide device further comprises a handle attached to the housing. In a preferred embodiment, the rotating guide device further comprises a stabilization means forming a secure anchor point between the device and an epicardial surface. In a preferred embodiment, the stabilization means of the rotating guide device comprises a flexible bellows portion integral with the housing portion thereby forming an evacuable chamber extending somewhat beneath the lower surface of the housing portion when placed adjacent the epicardial layer, and a vacuum port in communication with a vacuum applying means such that when the rotating guide device is placed adjacent to the epicardial layer, the evacuable chamber can be evacuated, thus providing a vacuum seal between the rotating guide device and the epicardial layer. In a preferred embodiment, the stabilization means of the rotating guide device comprises the guide needle means. In a preferred embodiment, the rotating guide device further comprises a laser delivery means advancing mechanism mounted within the handle. In a preferred embodiment, the rotating guide device laser delivery means advancing mechanism consists of a laser delivery means retaining means and an actuator wherein the laser delivery means retaining means holds the laser delivery means in a secure position within the handle and the actuator allows the laser delivery device to be advanced and retracted a predetermined distance through the handle. In a preferred embodiment, the rotating guide device laser delivery means advancing mechanism comprises an electric motor to advance the laser delivery means a predetermined distance. In a preferred embodiment, the rotating guide device rotating head means comprises a worm gear assembly. In a preferred embodiment, the rotating guide device handle portion is elongated in the shape of a hand wand for convenient manual control, the elongated handle having a proximal end through which a laser delivery means can be introduced into the handle portion, the handpiece further comprising a manifold for guiding the laser delivery means from the handle portion to the head means and into the hollow tubular opening of the guide needle means.

A guide needle for forming branched TMR channels comprising a hollow tubular body terminating in a distal tip curved to deflect a fiber optic laser delivery means mounted therein.

Numerous other advantages and features of the present invention will become readily apparent from the following detailed description of the invention and the embodiments thereof, from the claims and from the accompanying drawings.

BRIEF DESCRIPTION OF THE DRAWINGS

FIGS. 17–21 are views of a preferred embodiment of a rotating needle TMR handpiece of the present invention.

FIGS. 23–28 are representative illustrations of preferred embodiments of rotation drive devices of the present invention.

DETAILED DESCRIPTION OF THE PREFERRED EMBODIMENT

As described above, TMR is a process of introducing holes, channels or small tunnels into and through parts of the myocardium and the epicardial and/or endocardial surfaces.

The present invention is intended for use with any medical laser. In particular, the Holmium laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers, rods, mirror configurations and other laser delivery means are well described and will be useful in practicing the methods of this invention. It will also be understood that the preferred methods of the present invention are performed using the novel and unique devices described herein as well as any conventional mechanisms enabling angling or rotation of the fiber optic tip to effect creation of the branched channels.

Preferred Channel Geometries

Prior art channels are generally single, straight pathways. The contiguous branched channels of the present invention are communicating channels. The communicating channels may be straight, curved in one or more directions, or have internal corners of essentially any radius of curvature. While certain channel geometries will of course be more advantageous, either in terms of efficacy, length of time to perform the procedure, degree of complication of equipment required, skill level of surgeon, etc., virtually any channel geometry could in fact be produced in the heart. It will be understood that while the channels described herein as well as the methods for producing them are contemplated as originating at or just below the epicardial surface, they will generally continue through the myocardium and through the endocardium, although the channels could terminate at some point within the myocardium, providing thereby a "stimulus". All such "channel" embodiments will be expressly incorporated herein unless otherwise expressly delimited by specific limiting language, and the holes or channels contemplated will be primarily through both the myocardium as well as the endocardium.

Figure 1:
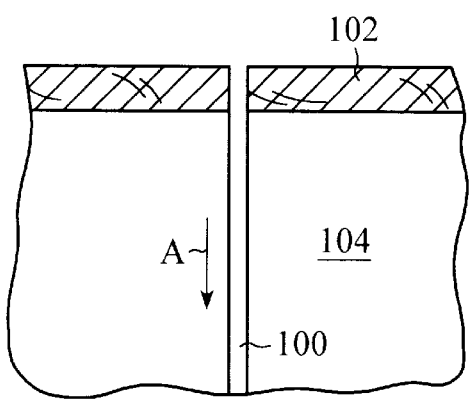
FIGS. 1–9 are channel geometry diagrams representative of cross-section views of channels through the myocardium embodying principles of the present invention.
Figure 2:
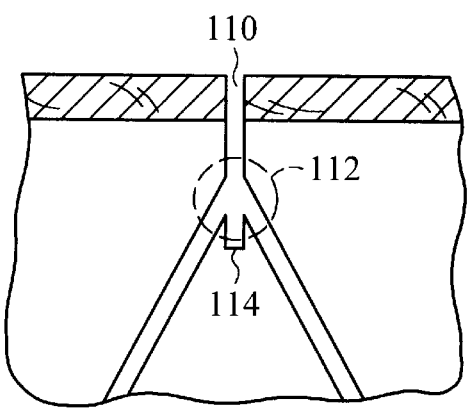
Figure 3:
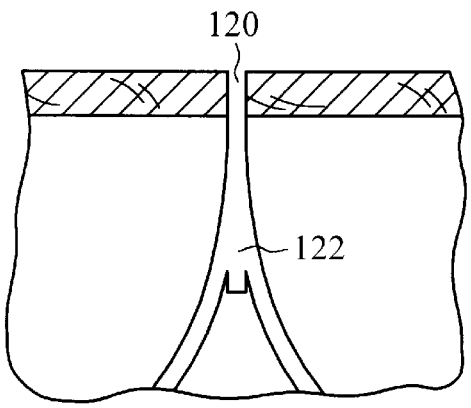
Figure 4:
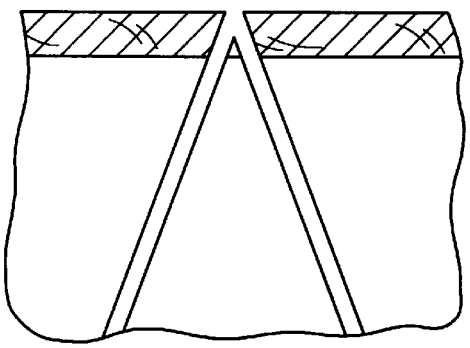
Figure 5:
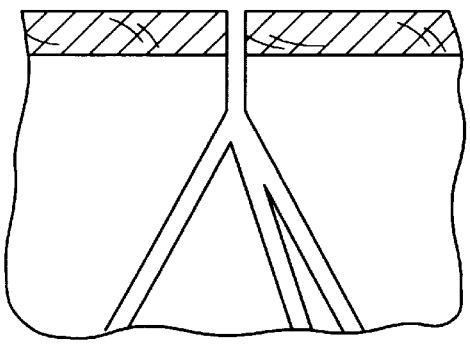
Figure 6:
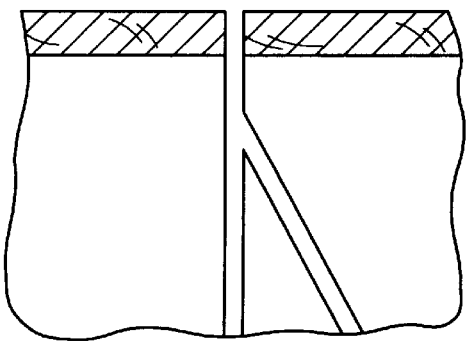
Figure 7:
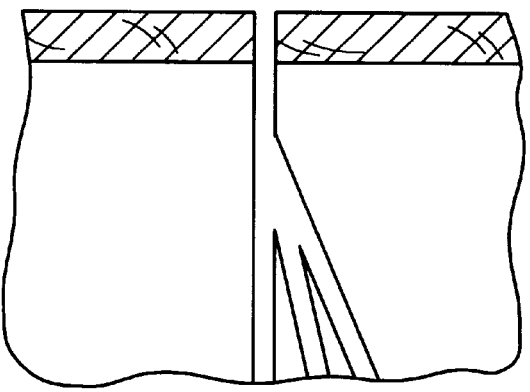
Figure 8:
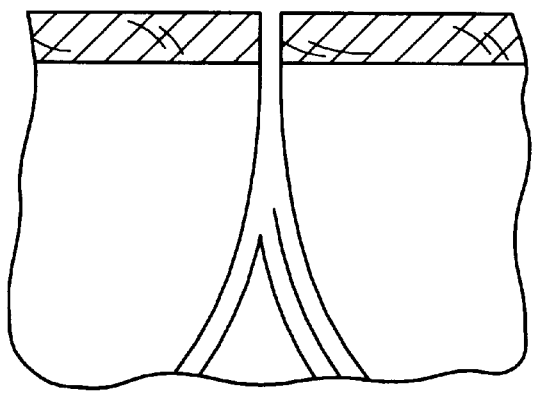
Figure 9:
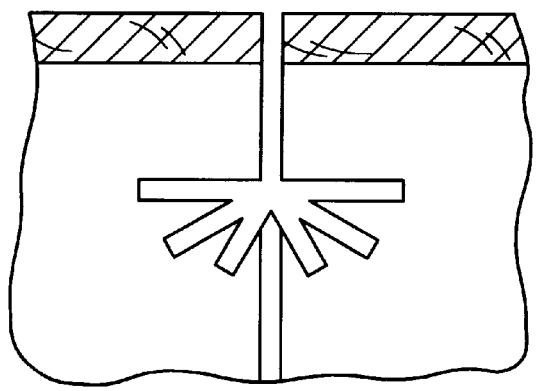

FIGS. 1–9 are channel geometry diagrams representative of cross-section views of channels through the myocardium embodying principles of the present invention. FIG. 1 shows a conventional channel 100. The channel develops along a direction or axis A essentially normal to the epicardial surface 102 of the heart into the myocardium 104. In FIG. 2, the "2D inverted Y" channel has one opening 110 at the epicardial surface. The channel is symmetrical and easily adaptable to a 3D geometry. There is a potential for creating a large cavity at the junction 112, for example, by extending the central branch 114 slightly below the junction, which will provide a channel with a larger void volume, eliminate sharp angles and increase the potential for enhanced blood circulation therethrough. Furthermore, according to fluid mechanics the pressure drop in blood flowing from the inside of a heart chamber through the endocardium along a channel through a first branch and through a second branch will be less if the cavity is larger or the degree of angle in the corners is less. It will be understood, therefore, that the term "cavity" will include the entire region between the opening in the epicardial surface and the bottom of the central branch, including the central branch and the junction with the two or more branches depending therefrom. In FIG. 3, the "curved inverted Y" branched channel also has one opening at the epicardium surface 120, and can be symmetric and adapted to a 3D geometry. Additionally, a larger cavity 122 may be provided near the junction of the main channel, resulting in a reduced risk of causing thermal damage in the junction region.

It will also be understood that the depth of penetration of the initial channel below the epicardial surface can be varied by the surgeon or by operating options of the devices of the present invention. The initial part of the channel can be very short, such that the junction between branches depending therefrom is closer to the epicardial surface or is deeper within the myocardium. Operator adjustments can be made to the depth of penetration of the guide needle or laser delivery means by provision of a depth stop means. Such depth stop means will control the subepicardial distance through which not only the guide needle or piercing needle can be advanced but also the distance through which the laser delivery means can be advanced. Of course, as will be apparent, the degree of rotation of the guide needle or other piercing means can be adjusted infinitely or according to certain pre-set indexed rotation stops or indents.

The following table is a list of the names associated with various channel geometries. It will be understood that these names are intended to be descriptive of certain embodiments and are not, therefore, limiting in any way.

| FIG. | Preferred Channel Geometries |
|---|---|
| 1 | straight or conventional |
| 2 | 2D inverted Y |
| 3 | 2D curved inverted Y |
| 4 | 2D or 3D inverted V |
| 5 | 3D squid shape |
| 6 | 2D twig |
| 7 | 3D twig |
| 8 | 3D curved, inverted Y |
| 9 | 2D or 3D capillary channel |

An important consideration when forming a plurality of channels having a plurality of branches is the overall rise in temperature of the surrounding tissue. It will be understood that while a great number of branches could actually be lased, all at different angles to the axis normal to the surface of origin, the heat produced may be damaging to the tissue surrounding the channels, especially in the area of the cavity or other junction between individually-bored or lased channels. Increasing the delay between the boring of individual channels would of course allow for dissipation of excess heat.

Another consideration is direction of blood flow within the heart and coronary arteries and placement of the channels. Since there is flow through the heart and coronary arteries, at least during various stages of the heart's cycle, a pressure gradient can be found through the heart and through individual chambers. Providing channels with multiple openings in the endocardium aligned with or oriented in the direction of blood flow will increase the blood flow through the patent channels.

It will be understood that the devices of the preferred embodiments of the present invention are particularly suited to both open heart surgery as well as the more recently popular minimally invasive surgery (MIS) techniques. It will be understood that in MIS procedures, since reducing the size of the opening in the chest cavity is one goal, devices must be appropriately designed to allow for as much control as possible while minimizing the size of access pathways to the heart.

Figure 10A:
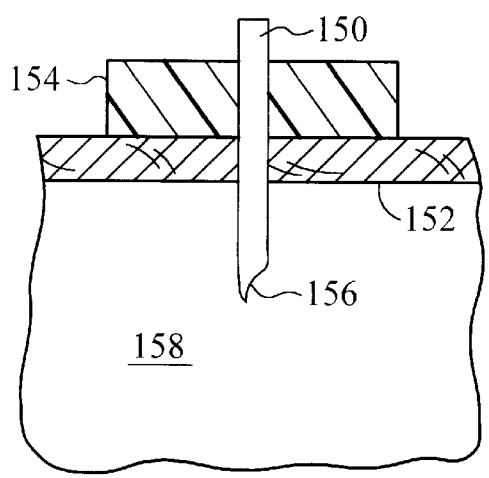
FIGS. 10A–10D are representations of a preferred embodiment of the device and method of use of the present invention.
Figure 10B:
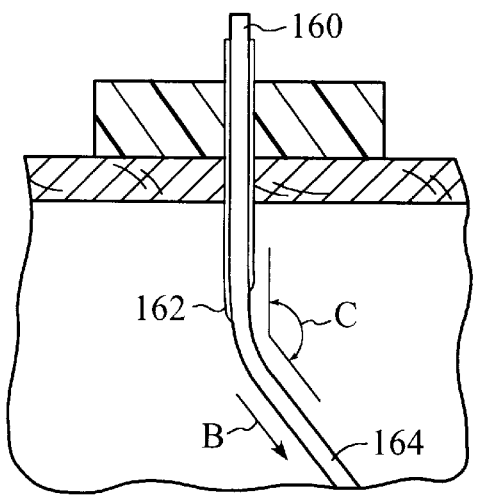
Figure 10C:
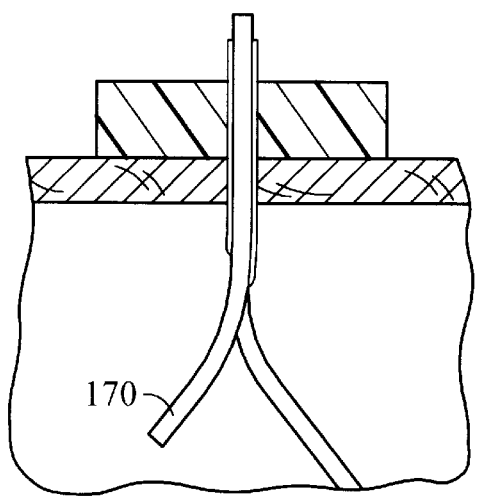
Figure 10D:
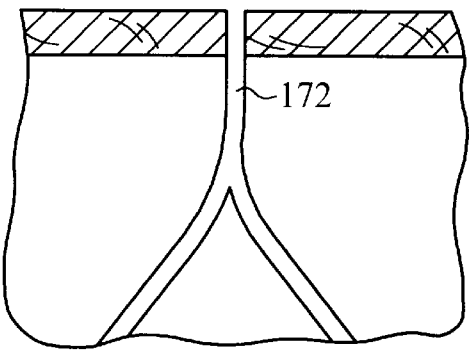

FIGS. 10A–10D are representations of a preferred embodiment of a device and method of use of the present invention for using a needle to pierce the epicardium. In FIG. 10A, the needle 150 is inserted through the epicardial surface 152, optionally through a guide block 154, mandrel or other stabilizing means. The curved needle has an opening 156 which can be oriented in a predetermined direction with regard to the myocardium 158 to be vascularized. In FIG. 10B, a laser delivery means 160, such as a fiber or fiber bundle is introduced through the lumen of the needle. A curvature which initiates with the distal tip 162 of the needle is maintained by the optical fiber or fiber bundle resulting in a first curved channel 164 being formed along a first axis B, forming an angle C with the normal to the epicardial surface. As shown in FIG. 10C, the laser delivery means is retracted into the needle, the needle is rotated thus orienting the opening away from the first channel, and the laser delivery means is again advanced to form a second curved channel 170. In FIG. 10D, the laser delivery means and needle have both been removed and the resulting branched channel 172 remains. The method of forming the channel can be modified as the surgeon prefers, but will generally comprise a combination of fiber advancement and laser delivery. It will be understood that a cavity below the epicardial surface can be formed by directing an extra pulse or two of laser energy at the junction of the branches. This cavity will increase the patency of the channel as well as the blood flowthrough capacity. Further, it will be understood that a single optical fiber as well as a fiber bundle can be used, and the fiber or bundle preferably includes a bias member to facilitate flexibility and assist in navigation through the curved needle. A bias member may include, for example, a piece of nitinol or other malleable or memory wire within the bundle of fibers or a heat-treated plastic material piece or jacket around the bundle preset in an arc. A pre-bent needle also reduces friction and improves tactile sensation as the fiber is advanced.

Rotating Guide Needle

Figure 11:
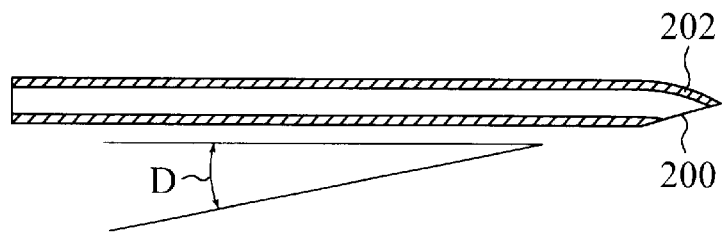
FIGS. 11–14 are cross section and slight isometric views of guide needles used in the preferred embodiments of the method and devices of the present invention.
Figure 12:
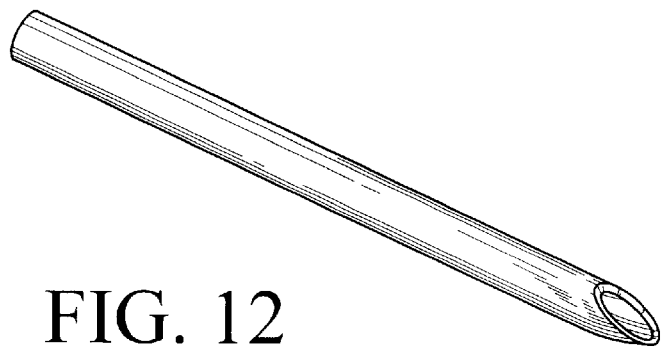
Figure 13:
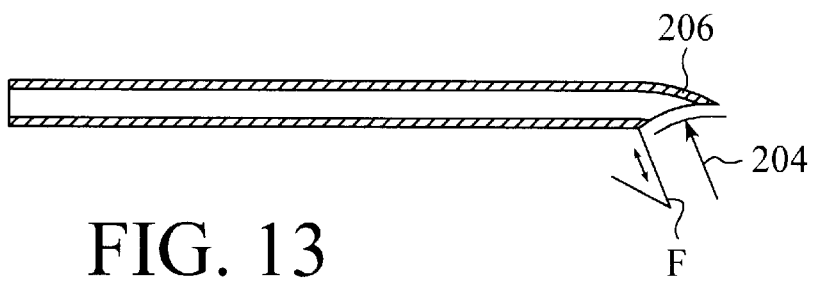
Figure 14:
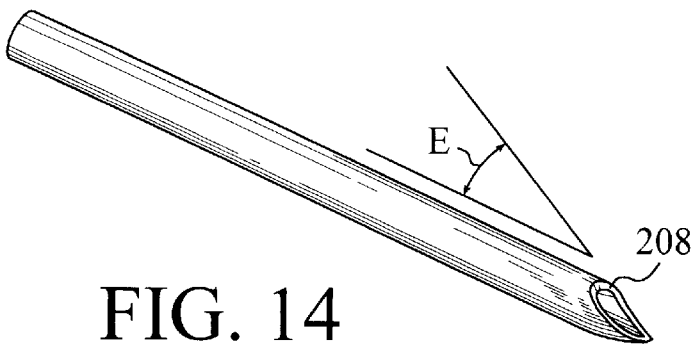

FIGS. 11–14 are cross section and slight isometric views of guide needles used in preferred embodiments of the method and devices of the present invention. FIG. 11 is a cross section view of a needle with a straight cut end opening 200 opposite the curvature 202 of the distal tip. FIG. 12 is a slight isometric view of the same embodiment. FIG. 13 is a cross section view of a needle with a conical cut end opening 204 opposite the curvature 206. FIG. 14 is a slight isometric view of the same embodiment. It will be understood that the distal end of the needle will be defined as the end from which the laser delivery means extends so as to lase a channel into the myocardium and comprising the conical or flat cut piercing point and curvature for deflecting the distal end of a laser delivery means. The proximal end of the guide needle will be understood to refer to the end into which the laser delivery means enters the guide needle. Typically, needles are cut from suitable stock material or otherwise manufactured. The radius at the end which deflects the laser delivery means at an angle may be formed by rolling the material over a ⅜ or ½ inch mandrel or other form. Typically, the angle D formed between the straight cut end plane and the needle axis, or the angle E formed between the conical cut plane and the needle axis, will be, in a preferred embodiment, between about 3–10°. The conical cut end tip can be formed by starting with a flat cut end tip, producing a bend at the end of the needle using a mandrel, spinning the needle about it's central axis and turning the end cut surface over a radius of curvature to form arced surface 208 having a radius of curvature F. This can be done with a dremel tool or other mill, lathe, etc. It will be understood that the internal shoulder of the opening of the needle near the laser delivery deflecting curvature will be rounded or otherwise smooth enough so as not to damage or bind the fiber or fiber bundle upon insertion or extraction. Another method of forming an efficient piercing tip is to form the bend in the tip of the needle, spin the needle about an axis slightly off the central axis of the needle by between about 6–8°, and then grinding the end cut surface with a conical shaped surface. This provides a more durable, efficient piercing needle tip. In the preferred embodiments, due to the fact that the outside diameter of the fiber or fiber bundle will necessarily be smaller than the inside diameter of the needle tip to be efficiently extended and retracted, the theoretical fiber deflections by the needle tips will be between about 25–30° whereas the resulting actual bend of the laser delivery device will be less than that.

In a preferred embodiment, the guide needles of the present invention have heating means so that the tip of the needle is hot as it pierces the surface of the epicardium to reduce or eliminate bleeding by cauterizing the tissue opening of the pierced channel. Thereafter, as the laser delivery means is urged through the needle and is used to lase a channel or channels into the myocardium, excessive bleeding will not interfere with visibility in the area. The heater means may include a small resistance heater to heat the tip of the needle by passing an electrical current through it. Another embodiment uses an absorptive element on the needle, such as a stainless steel tip, preferably at or near the fiber deflecting curvature, so as to absorb a part of the transmitted laser energy to heat the tip sufficiently. Other heater means will be known to those skilled in the art.

Pivot-point Guide Block

Figure 15A:
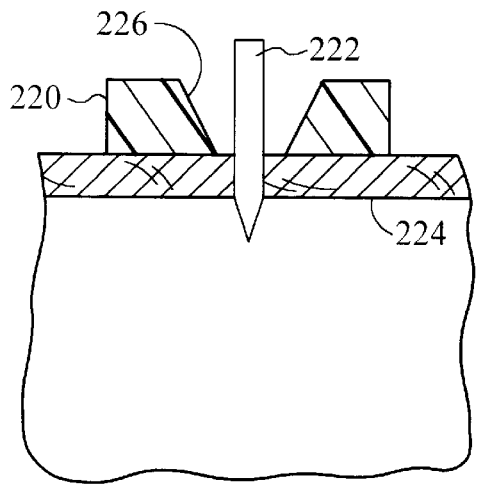
FIGS. 15A–15D, 16A–16B are illustrative representations of a pivot-point and flex-joint guide block device and method of use of a preferred embodiment of the present invention.
Figure 15B:
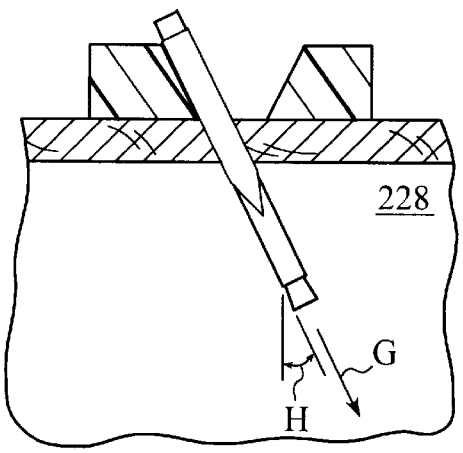
Figure 15C:
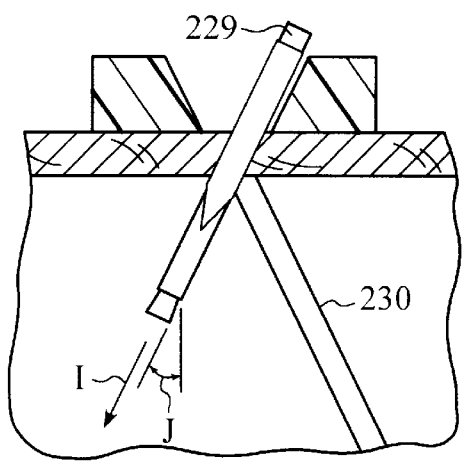
Figure 15D:
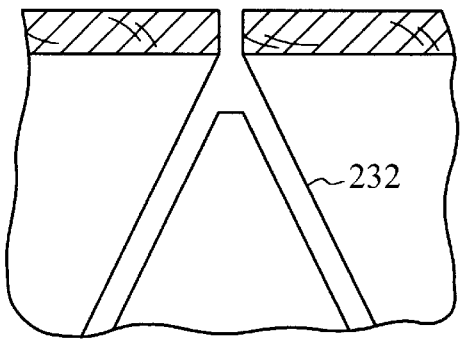

FIGS. 15A–15D are illustrative representations of a pivot-point guide block device and method of use of a preferred embodiment of the present invention. The guide block 220 is placed onto the epicardium and a needle 222 is advanced until it pierces the epicardial surface 224. The guide block has a frustoconical internal bearing surface 226. As the needle and fiber mounted therein is tilted to one side as in FIG. 15B, it is brought to bear against the bearing surface to point downward into the myocardium 228 in direction G, at an angle of H with the normal to the epicardium. In this embodiment, a needle which does not deflect the delivery end of the laser delivery means can be used. In FIG. 15C, the fiber 229 or other delivery means has been retracted and the fiber was tilted to another orientation biased against the bearing surface. In this position, the fiber is again advanced and a second channel can be formed in a direction I at an angle J with respect to the first branch 230. The resulting multi-branch channel 232 will be formed thereby originating just below the epicardial surface. This "pivot-point" concept can be used with a rotating needle device, described below, to create 2-dimensional or 3-dimensional branched channels. Alternatively, the guide block may be used as support for a laser piercing apparatus in which case the laser tip is rotated to create a double channel with the block acting as a flex or pivot joint.

Figure 16A:
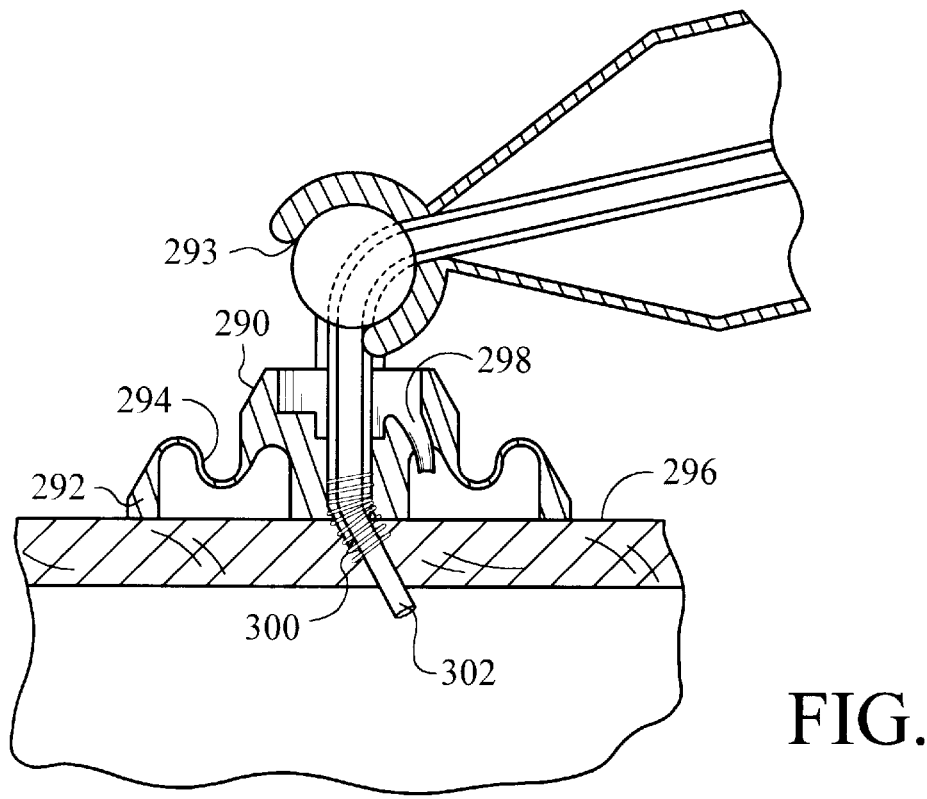

FIG. 16A is a cross section view of a guide block with flex-joint tip and bellows for vacuum-assisted stabilization of the device. The guide block has a housing portion 290 with a flexible bellows 292 extending downward and outward from the perimeter of the housing. Above the guide block there is a flex joint 293. This joint, for instance a ball and socket-type joint, allows the laser delivery means to be positioned at an angle for access to areas where the delivery means cannot be positioned upright prior to channeling through the myocardium. A thin-walled portion 294 of the bellows will be made of rubber or some other flexible material. The bellows-equipped guide block sets on top of the epicardial surface 296. As a vacuum is applied to the inside of the bellows, through a vacuum port 298 in a preferred embodiment, the thin-walled portion of the bellows collapses, holding the bellows portion firmly secured to the epicardial surface. A flex-joint tip 300 is provided at the distal end of the laser delivery means path. An optical fiber 302, fiber bundle or other laser delivery means can then be extended through the flex-joint tip and used to lase a branch of a channel into the myocardium. Such vacuum-assisted apparatus and procedures are more fully described in co-pending U.S. patent application Ser. No. 08/628,849 filed Apr. 5, 1996, now U.S. Pat. No. 5,738,680.

Based on the foregoing description of the rotating guide block and the pivot-point guide block, it will be understood that the guide block equipped with a bellows can have an internally rotating portion or other means, to be described below, to re-orient the flex joint tip to create a second branch of the original channel. Furthermore, a guide needle could be placed at the distal end of the laser delivery means path such that when a vacuum force is applied the collapsing bellows drives the tip of the guide needle through the epicardial surface at a predetermined angle to the epicardial surface and to other channels. It will be understood that the bellows with suction attachment for maintaining the laser delivery means (or guide block or pivot block or other rotating means) is but a single stabilizer means for attaching the device to the heart at a given position during the procedure of lasing an individual channel. As the heart beats this suction device or other stabilizer means assists the surgeon to counteract the beating heart's motion. Individual practitioners may find that the stabilizer means is especially useful in minimally invasive surgical procedures, as opposed to open heart procedures, wherein locating a device precisely adjacent a specific region of the epicardium and holding it there during the procedure may otherwise be difficult. The stabilizer means will also include an external retractor or clamp-type feature such that the target spot is held in place but allowing the mass or greater bulk of the heart to move freely.

Figure 16B:
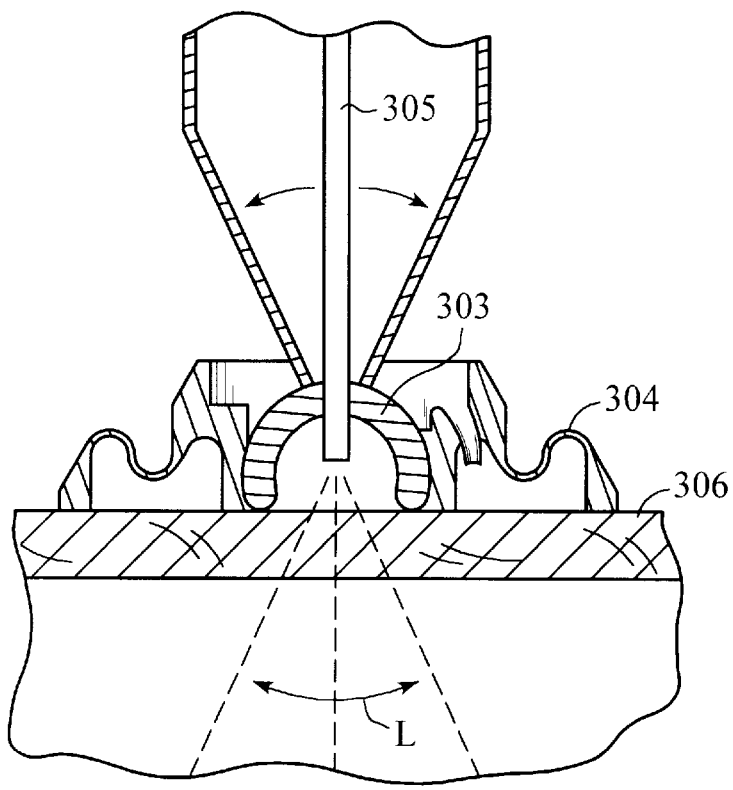

FIG. 16B is a cross section view of a guide block with flex joint and bellows for vacuum-assisted stabilization of the device. In this embodiment, the flex joint 303 is located within the flexible bellows 304. In this alternate embodiment, the flex joint for rotating the handle portion is located nearer the surface of the heart and the flexible tip is omitted. A needle 305, or guide tube, extends to a position just above the epicardium 306. In this way, a laser delivery device such as an optical fiber can approach the epicardium and bore holes therein at any angle within a given range of angles L with respect to the normal to the epicardial surface.

Rotating Needle TMR Handpiece

FIGS. 17–21 are views of a preferred embodiment of a rotating needle TMR handpiece of the present invention used to facilitate the formation of communicating channels. FIG. 17 is a graphic representation of the method of use of a handpiece of the present invention. The handpiece 310 can be held by the surgeon with one hand. An opening is made in the chest cavity using a conventional method and the head portion 312 is placed onto the heart 314 at the desired position. The head portion serves the purpose of a guide block in that the head portion can be positioned and secured to the heart with or without vacuum assistance. The head portion also may contain a guide needle. A thumbwheel 316 is used by the surgeon to advance the fiber or fiber bundle into the channel being created. A preferred embodiment also comprises an internal rotating retaining portion, explained below, which rotates after the fiber has been advanced, a channel created and the fiber and/or needle extracted.

FIG. 18A is a top isometric view of a preferred rotating needle handpiece of the present invention. The handpiece comprises a handle portion 320 and a tail portion 322. A thumbwheel 316 is used for advancing the fiber, bundle or other laser delivery means. A neck portion 324 is joined to the handle portion and may include a pivoting junction 326. As the fiber extends from the tail, through the handle portion and into the neck portion, the fiber is directed into a manifold 328 in order to effect the change in direction necessary to direct the optical fiber or bundle out of the head portion. It will be understood that the manifold structure could be manufactured integrally with the construction of the neck and head portion, such as by an extrusion or injection molding process. Such J-grip TMR apparatus is more fully described in co-pending U.S. patent application Ser. No. 08/607,782 filed Feb. 27, 1996, now U.S. Pat. No. 5,713,894.

Figure 18B:
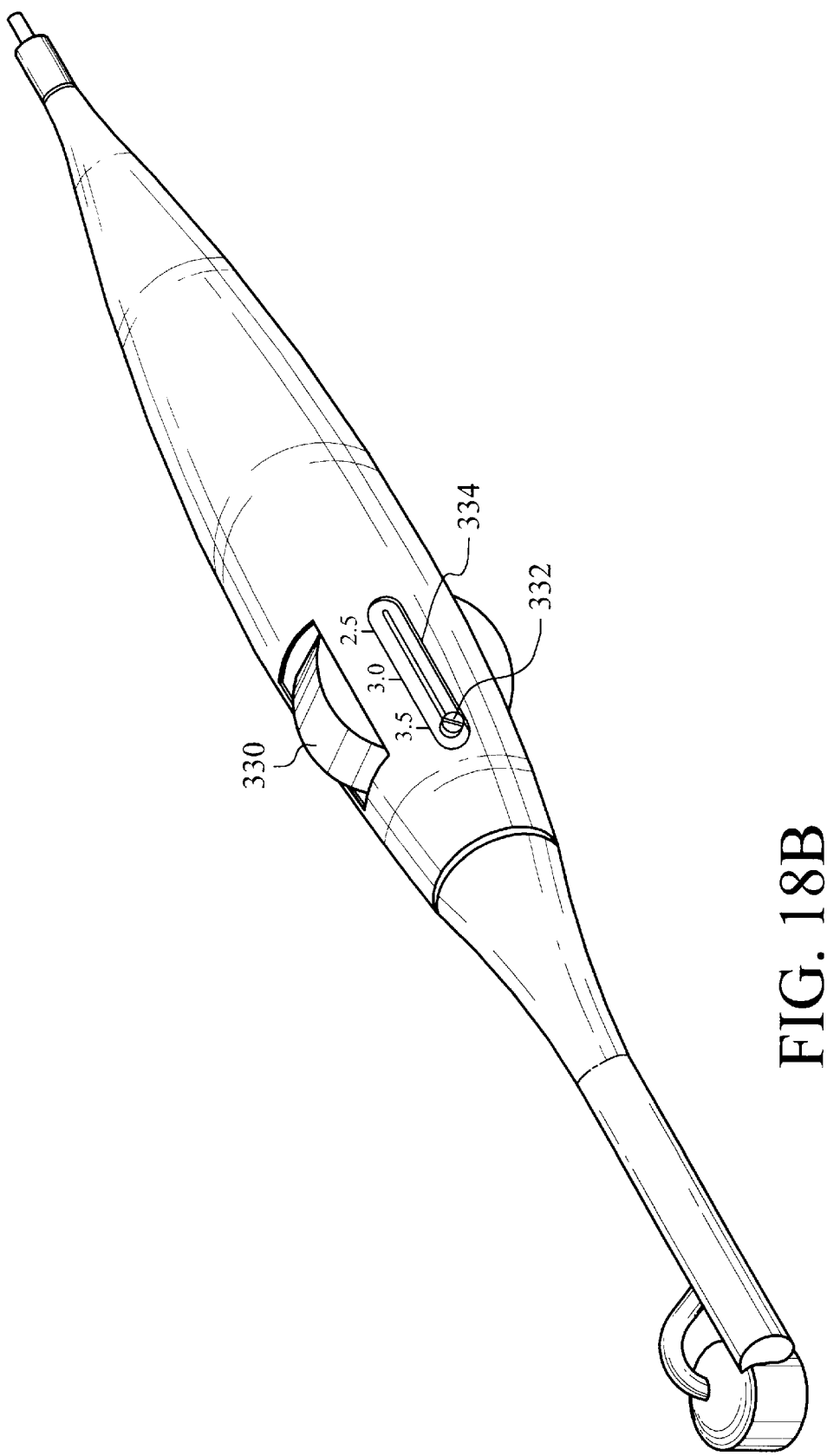

FIG. 18B is a top isometric view of a preferred rotating needle handpiece of the present invention with a fiber depth adjustment. As in the previously disclosed embodiments, a thumbwheel 330 is used to advance a laser delivery means, such as an optical fiber, through the handpiece. The distance which the fiber is advanced is controlled by a laser delivery means side slider-type depth adjust means 332. The maximum depth of the channel which is to be created by the handpiece can be set precisely and conveniently by locating the side slider at the appropriate axial position, as indicated by a scale or other reference means 334. In a preferred embodiment, the slider mechanism controls, and visually shows, the depth the fiber may be advanced, and adjusts the depth stop control. It will be understood that the handpiece may have a single-sided or a double-sided slider depth adjust means. Furthermore, other means for adjusting the depth of advancement of an optical fiber or other laser delivery means through the handpiece will be apparent to those skilled in the art.

Figure 19:
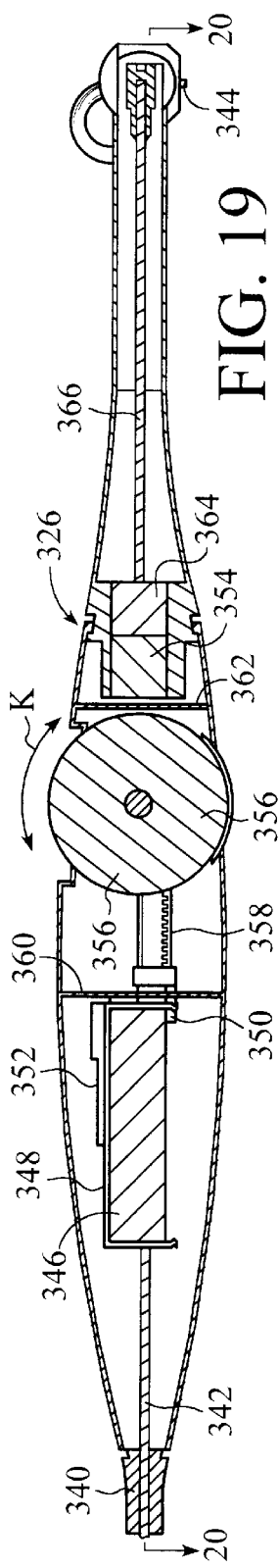
Figure 20:
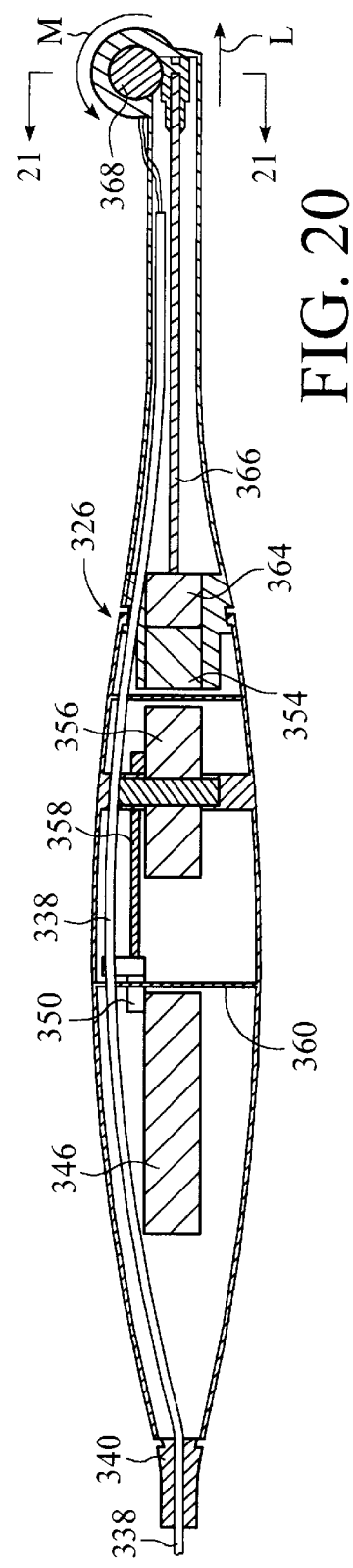

FIG. 19 is a side elevation view of a preferred rotating needle handpiece of the present invention and FIG. 20 is a top sectional view of a rotating needle handpiece of the present invention taken through section 20. It will be understood that the optical fiber 338 or other laser delivery means will enter at the proximal end 340 of the device, travel through a guide tube 342, and exit a guide needle 344 at the distal end of the device. In a preferred embodiment, a small battery 346 seated in a battery cradle 348 and operated by a micro switch 350 will power a circuit board 352 and needle rotating motor 354. Manual operation of the thumbwheel 356 will advance and retract the optical fiber or other laser delivery means coupled to a rack portion 358—individual gears on the thumbwheel engage the geared rack portion. Alternatively, fiber advance can be automated using a motor. A proximally located bulkhead 360 and a distally located bulkhead 362 are used to mount the internally disposed fiber advance mechanism as well as the head rotating mechanism in the TMR handpiece or wand. In a preferred embodiment, the head of the TMR wand is positioned on the heart muscle such that a guide needle pierces the epicardial surface at the intended channel site. The laser delivery fiber is advanced, utilizing the thumbwheel, as a channel is lased into the myocardium. The thumbwheel is moved in the direction shown by double-headed arrow K. It will be understood that the thumbwheel portion can be manufactured to directly advance the fiber without drive reducing gear, or conventional gear reduction can be utilized so as to advance the fiber a predetermined distance in response to a predetermined degree of angular rotation. In the automated embodiment, the thumbwheel is an electrical actuator with contacts which will complete an electrical circuit to move the fiber in the desired direction. The precise relationship between the degree of longitudinal motion and angular rotational movement can be selected as desired, with the precise engineering known to those skilled in the art. Once the first branch of the channel has been created, the thumbwheel will be used to retract the fiber. Thereafter, the guide needle can be re-oriented. Rotation of the guide needle can be actuated by control circuitry in response to movement of the thumbwheel to its rearmost position in which case the needle rotation motor is in a circuit with the thumbwheel. Alternatively, a separate switch can be installed on the handle or other portion of the TMR wand to control the angular rotation of the TMR head portion and guide needle. In a preferred embodiment, the guide needle rotation motor is coupled to a gearhead 364. A shaft 366 extends through the neck of the handpiece, from the gearhead to a rotating portion 368.

Figure 21:
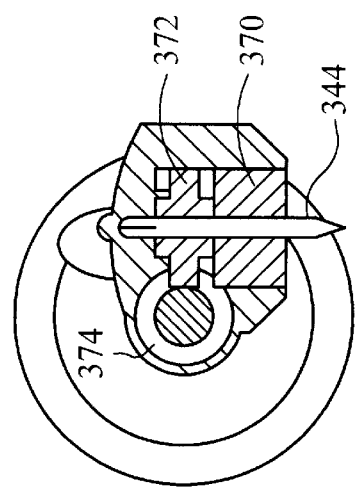

FIG. 21 is a detail front sectional view of a rotating needle handpiece of the present invention taken through section 21. As described, the device comprises both a fiber advancing mechanism and a guide needle rotating means, optionally and preferably in various embodiments, with associated electronics, sensors, stops, actuators, power sources, etc. The needle holder 370 is integral with a pinion gear 372 which is acted on by a worm gear 374. As the worm gear is advanced in direction L, the pinion gear 372 rotates with the needle holder 370 and the needle 344, all three in direction M. As described, the preferred embodiment has an automatic needle rotation and angle extending synchronization electronics system, such that the thumbwheel comprises an actuator and sensor to detect the length of fiber advancement. Controllers rotate the needle a predetermined angular degree.

Figure 22:
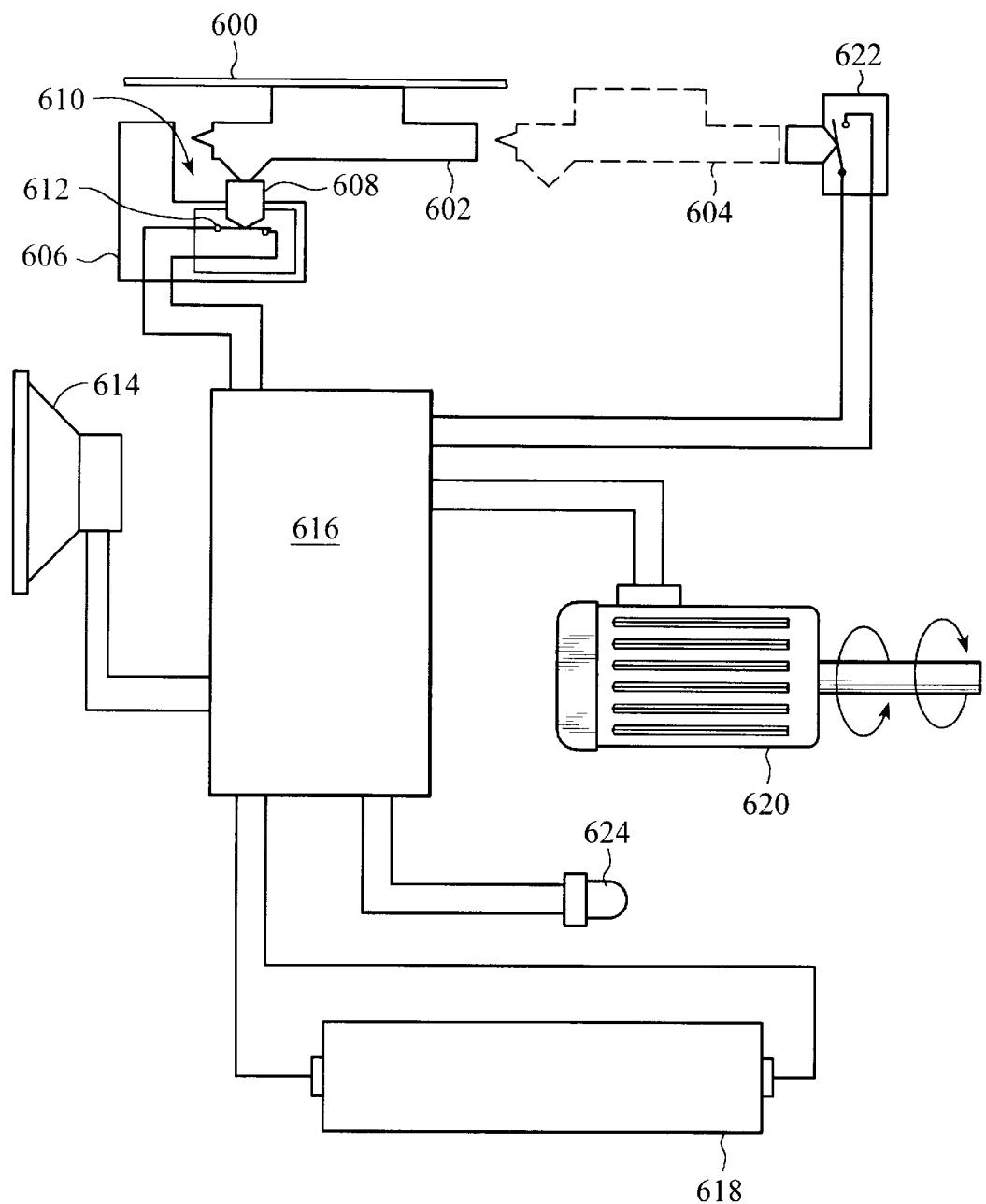
FIG. 22 is an electronics block diagram for a rotating needle handpiece of the present invention.

FIG. 22 is an electronics block diagram for a rotating needle handpiece of the present invention. For representative purposes, the optical fiber or fiber bundle 600 is shown attached to a fiber advance mechanism 602 shown in a forward position. The switch can also be moved into a rear position 604. A switch block 606 is adjusted such that before a mechanical or other linkage 608 on the fiber advance mechanism reaches a mechanical depth stop 610, a sensor 612 at a certain position will activate an audible alarm 614. This audible alarm will advise the surgeon with regard to the depth of penetration of the optical fiber so as to achieve uniform depth of penetration and precision in channel formation throughout the procedure. The alarm could also be visual or sensory, or otherwise integrated with other intelligent control. Associated control electronics comprise controller 616. This controller comprises a printed circuit board, pre-programmed, programmable or semi-programmable micro-controllers, other inputs or outputs, and other associated electronics. A power source 618 such as a battery is attached to the controller and provides power to the alarm as well as a small direct current motor 620. This small motor toggles forward and reverse depending upon a signal produced by a motor activation and toggle direction selection switch 622. This switch is activated when the depth adjust mechanism is in the rear position. A preferred embodiment utilizes a small motor rotation indicator LED 624 or other visual, sensory or audible indicator. The switches of the device are either mechanical, Hall effect, optical or other, with the motor current and voltage either predetermined or variable. Various types of alarms will be known to those skilled in the art including small lights, audible alarms, vibrating components, diodes, other electronic means or otherwise. It will be understood that while the preferred embodiment includes mechanical linkages, these mechanical components can be replaced with electronic or other actuated systems for fiber advance as well as needle rotation. An additional audible alarm may be provided at a different frequency to signal needle rotation.

Various embodiments for accomplishing rotation of the needle in the rotation drive will be known to those skilled in the art. Any mechanical head rotation means, for example rack and pinion assembly, worm gears, actuator rods, torsion springs, etc. will be adaptable to the present invention.

Finger-tip Operated TMR Device

FIGS. 23–28 are representative illustrations of preferred embodiments of rotation drive devices of the present invention designed to be held by one or two fingers with the remaining fingers and device acting as a heart retractor when used to approach the inaccessible posterior side of the heart. FIG. 23 shows a top perspective view of a finger-tip operated TMR device. It will be understood that the fiber 500 can be fed into and through the device either through a horn portion 502, other handle or support means particularly for TMR on the back side of the heart, or directly through an opening 504 on the upper portion 506 of the device. Opening 504 is particularly useful in high access areas and allows straight fiber advancement thereby reducing drag. In another embodiment of the present invention, the TMR device is held by one hand while the laser delivery means is inserted through the TMR device with the opposite hand or by an assistant. The hand used for insertion operates the laser advance mechanism trigger, such as a thumbwheel 508. The manual feed system also utilizes a finger-tip operated button 510 to effect needle rotation. The low profile of the rotating handpiece is key for use in confined spaces. FIG. 24 shows a top perspective of a wrist-held finger-tip operated TMR device. While the fingertips are used in a described fashion to control a push-button, the device utilizes a strap portion 520 for stabilization and for freeing the rest of the fingers for retraction of the heart for posterior wall approaches.

Figure 25:
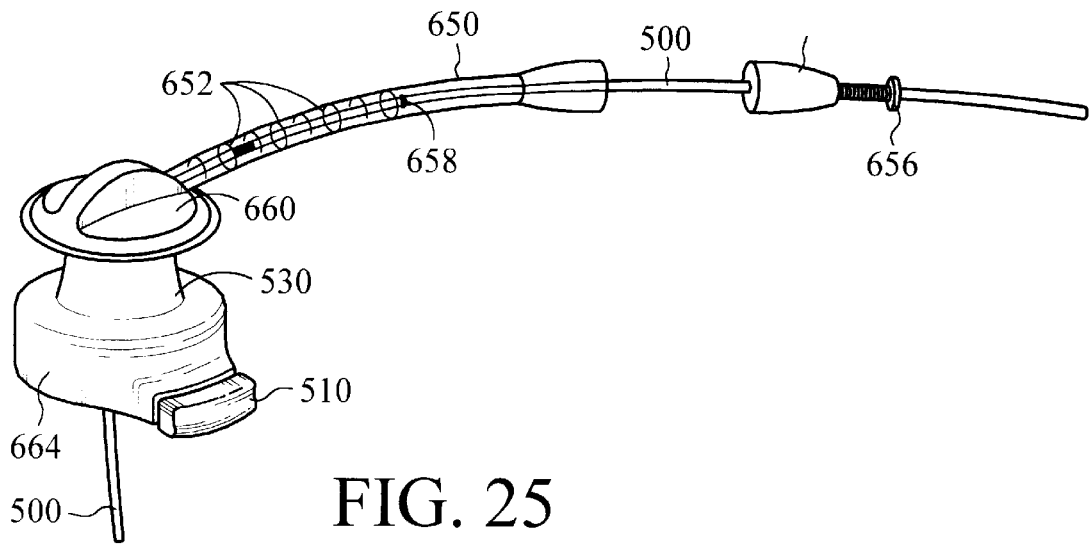
Figure 26:
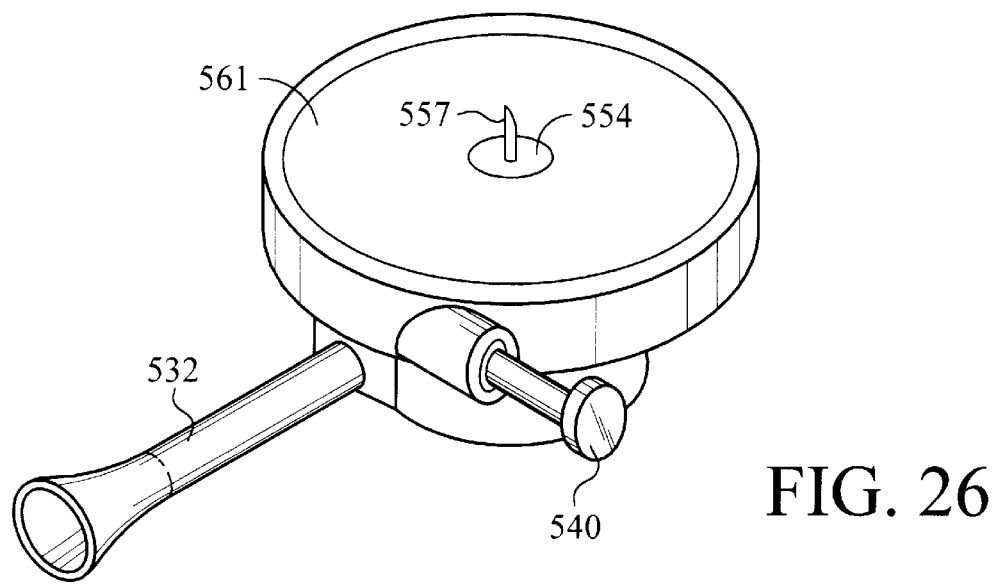
Figure 27:
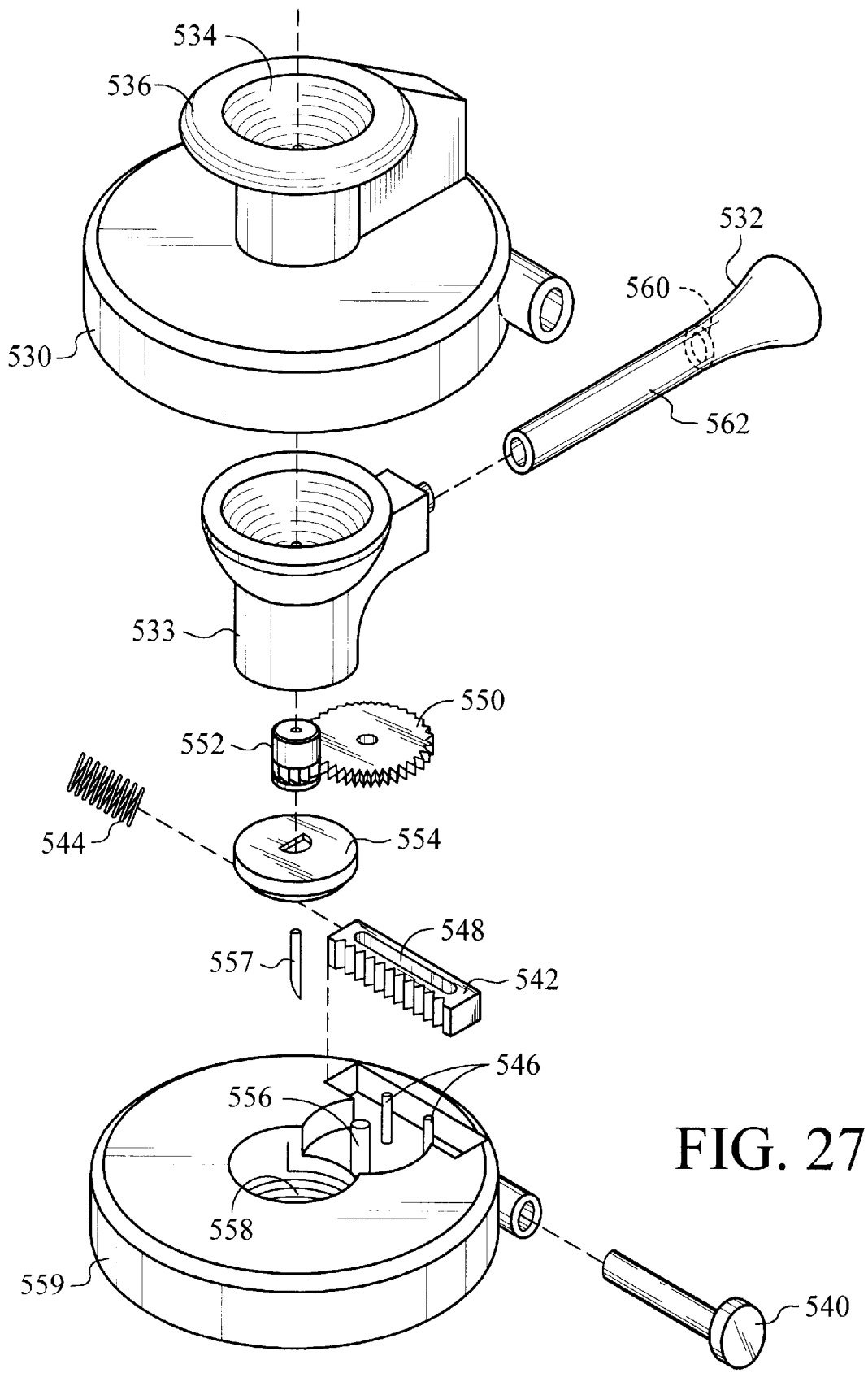

FIGS. 25–27 are upper, lower and exploded isometric views of two preferred embodiments of finger-tip operated TMR devices of the present invention. FIGS. 26 and 27 show a housing 530 or other protective covering is manufactured of a suitable, lightweight, autoclavable or otherwise sterilizable material with a suitable surface texture to allow the surgeon to grip the device during the procedure in the presence of blood or other fluids. A horn 532 or other hollow opening or extending structure, serves as a first path to feed an optical fiber through the device, through insert 533. A fiber or other laser delivery means can also be inserted into the device through conical portion 534 on the upper portion of the housing. The conical portion has a small hole on the inside through which the fiber can be advanced. In a preferred embodiment, the conical portion includes a flange 536 which serves to keep the device securely positioned in a surgeon's hand when the surgeons fingers are slid between the housing and the flange. The finger-tip controlled push button 540 is mounted inside the housing and engages with a rack 542 and a spring 544. When desired, depressing the push button moves the rack, retained in place on two pins 546 extending through slot 548, in an axial direction. The teeth of the rack engage reducing gear 550 which is mounted on pin 556. The teeth of the reducing gear engage with pinion gear 552. Rotating head 554, pressed onto or otherwise fixed to the pinion gear, rotates in unison with the gear assembly and with guide needle 557 retained therein. The rotating head rides in the center 558 of a chassis portion 559 of the device. It will be understood that the chassis portion serves primarily to retain the integrity of the assembly, as may be necessary. The overall dimensions of a preferred embodiment of the present invention is about 3 inches in diameter, about 4½ inches long to the end of the horn, and only about 1 inch tall, not including the slightly extending needle. The first opening 560, through the hollow tubular section 562 of the horn or other handle serves as a path to advance the fiber through the device.

The preferred single entry port embodiment shown in FIG. 25 also employs a finger or thumb activated needle rotation button or bar 510 set into the lower portion 664 of the housing 530 and is particularly suitable for minimally invasive surgery (MIS) procedures such as TMR from the posterior surface of the heart. Such posterior- and lateral-aspect procedures are more fully described in co-pending U.S. patent application Ser. No. 08/627,704 filed Mar. 29, 1996, now U.S. Pat. No. 5,725,523. A transparent or semi-transparent tube 650 with graduated markings 652 extends from the upper portion. In a preferred embodiment, this tube twists off forming an open side port. The device is held between the index and the middle fingers and the remaining fingers of the same hand are available for retraction and stabilization. A depth stop 654 is attached to the optical fiber or fiber bundle 500, the depth stop being adjustable with positioning means 656, such as a threaded clamping mechanism on the fiber, such that the maximum depth of penetration of the laser delivery means can be controlled. The depth stop is positioned at a predetermined position on the optical fiber. Additionally, a detent 658 such as an integrally formed bead or other affixed component prevents the optical fiber from being fully retracted from the device. The graduated markings on the flexible or semi-flexible tube serving to provide the surgeon with a visual indicator as to the depth of penetration during channel formation. The upper portion 660 will pivot about joint 662 such that the surgeon can efficiently position the lower housing 664 without restriction caused by a predetermined orientation of the laser delivery means. The rotatable needle may be retractable and scallops may be provided in the housing, and on the button, to facilitate gripping, and for other design purposes. Furthermore, it will be understood that the lower surface 561 of the TMR device may also be made of a non-slipping material such as textured metal or rubber, and may also have a dimpling or raised pattern thereon to facilitate secure placement of the device during operation.

Figure 28:
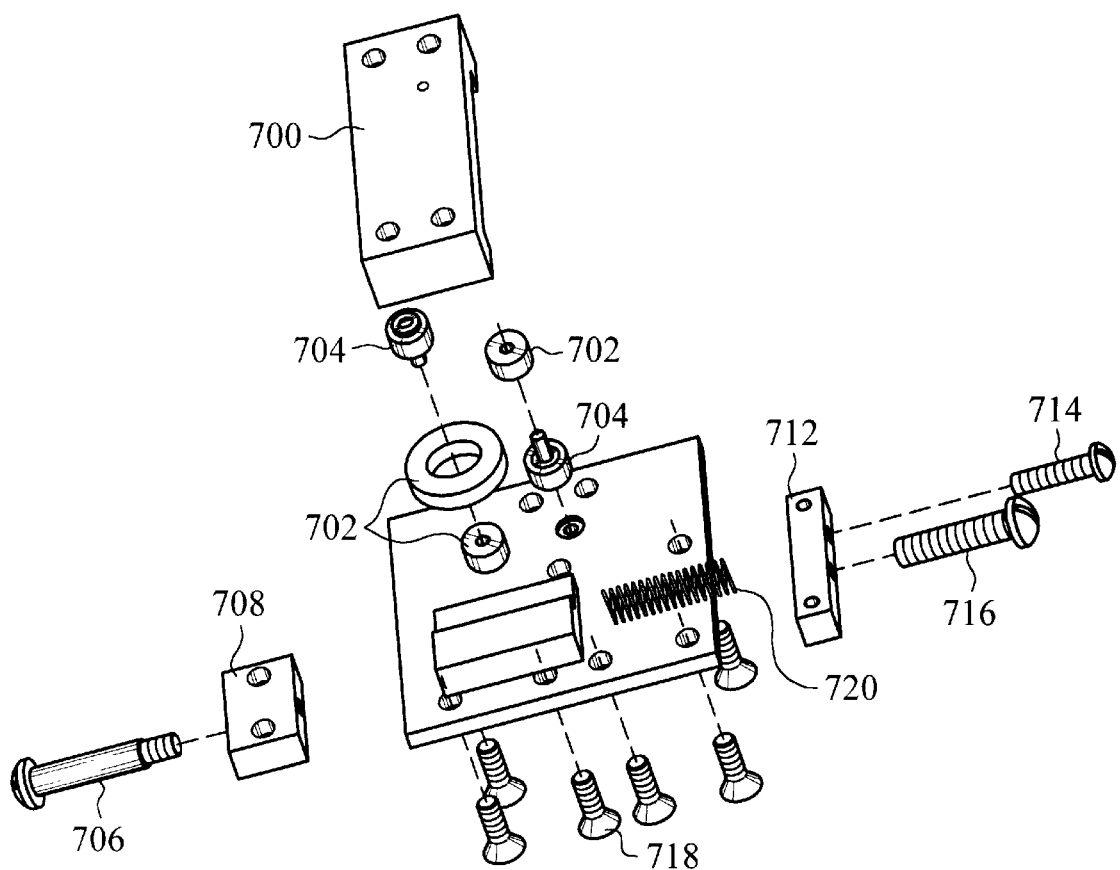

FIG. 28 is an alternate exploded view of the needle rotating mechanism gearbox of finger-tip operated TMR device of the present invention. A gear retainer 700 houses a plurality of gears 702 rotating about a plurality of axles 704. A button 706 is disposed inside a button retainer 708 such that it bears upon a rack gear 710. A mechanical stop element 712 also serves as a spring screw retainer. Stop screw 714 and spring tension adjustment screws 716 act upon the mechanical stop element and spring 720. A plurality of fasteners 718 hold the assembly together.

Various embodiments for accomplishing rotation of the needle in the rotation drive will be known to those skilled in the art. Any mechanical head rotation means, for example rack and pinion assembly, worm gears, actuator rods, torsion springs, etc. will be adaptable to the present invention.

It will be understood that any of the embodiments described herein in which a guide needle or other piercing means is followed by a laser delivery means, it will be an optional feature to provide a rotation interlock system. Such interlock system will prevent needle rotation before the fiber is retracted or otherwise withdrawn from the opening. This will prevent injury to the heart. The interlock will ensure that the guide needle will not rotate prior to withdrawal of the laser delivery means into at least the shaft of the needle.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A method for creating contiguous branched transmyocardial revascularization channels comprising:
   a) positioning a guide device having a rotating distal head in combination with a hollow piercing element having a curvature at a distal end, on an epicardial surface adjacent myocardium;
   b) piercing the epicardial surface with the piercing element to create an entry point;
   c) deflecting a laser energy delivery device through the curvature of the piercing element into myocardium at a predetermined angle with respect to the epicardial layer; and
   d) creating a first angled channel in myocardium.

2. The method of claim 1 further comprising:
   e) retracting the laser energy delivery device into the hollow piercing element;
   f) rotating the piercing element;
   g) advancing the laser energy delivery device into myocardium from the entry point to create a second channel.

3. The method of claim 2 wherein the rotating distal head is indexed with a predetermined number of angular positions and further comprising step h) repeating steps e) through g) and angling the distal end of the piercing element to a number of angular positions to allow the laser energy delivery device to deliver laser energy into myocardium at predetermined angles.

4. A method for forming angled myocardial revascularization channels comprising:
   a) positioning a distal tip of an apparatus having a distal rotating orientation member in combination with a curved hollow needle on a heart surface adjacent a preselected location of myocardium;
   b) perforating the surface to create an access opening;
   c) curving a distal end of a laser energy delivery device through the needle through the perforated surface into myocardium at a predetermined angle with respect to the surface; and
   d) transmitting laser energy from the distal end of the laser energy delivery device into myocardium.

5. The method of claim 4 further comprising step e) rotating the orientation member to form a multi-ended channel with the access opening.

6. The method of claim 4 further comprising step e) rotating the orientation member to form a plurality of channel branches from the access opening, having predetermined geometries extending into and through myocardium.

7. The method of claim 6 further comprising step f) directing laser energy into a junction of the plurality of channel branches to create a cavity.

8. The method of claim 4 further comprising a laser energy delivery device housed in and translatable through the apparatus and step b) perforating the surface with laser energy.

9. The method of claim 4 step b) perforating the surface mechanically with the curved hollow needle.

10. The method of claim 9 the apparatus further comprising a heating mechanism operatively coupled to the needle and further during step b) cauterizing the perforated surface opening.

11. The method of claim 4 the apparatus further comprising an automated advancing mechanism operatively coupled to the laser energy delivery device and during step c) advancing the laser energy delivery device automatically to a predetermined depth in the myocardium.

12. The method of claim 4 the apparatus further comprising a manual advancing mechanism operatively coupled to the laser energy delivery device and during step c) advancing the laser energy delivery device manually to a predetermined depth in the myocardium.

13. A method for forming multiple transmyocardial channels with a single entry point comprising:
   a) tilting a hollow piercing element and laser energy delivery device combination against a first surface of a guide device having a plurality of frustoconical internal bearing surfaces, said guide device placed on a heart surface adjacent myocardium;
   b) piercing the surface with the piercing element;
   c) advancing the laser energy delivery device through the piercing element to create a first channel in myocardium;
   d) retracting the laser energy delivery device into the hollow piercing element;
   e) orienting the piercing element against a second surface of the guide device; creating a second channel at an angle to the first channel in myocardium.

14. A method for creating contiguous branched transmyocardial revascularization channels comprising:
   a) positioning a guide device having a distal head in combination with a hollow piercing element having a curvature at a distal end, on a heart surface adjacent myocardium;
   b) inserting the piercing element through the surface and into myocardium;
   c) advancing and deflecting a laser energy delivery device through the curvature of the piercing element into myocardium at a predetermined angle with respect to the surface; and
   d) creating a first angled channel in myocardium.

* * * * *